US008293471B2

(12) United States Patent
Gregg et al.

(10) Patent No.: US 8,293,471 B2
(45) Date of Patent: Oct. 23, 2012

(54) APPARATUS AND METHOD FOR A CONTINUOUS RAPID THERMAL CYCLE SYSTEM

(75) Inventors: Derek A. Gregg, Barboursville, WV (US); Elizabeth E. Murray, Huntington, WV (US); Michael L. Norton, Huntington, WV (US); Justin T. Swick, Chesapeake, OH (US); Herbert Tesser, Huntington, WV (US)

(73) Assignee: Marshall University Research Corporation, Huntington, WV (US)

( * ) Notice: Subject to any disclaimer, the term of this patent is extended or adjusted under 35 U.S.C. 154(b) by 1163 days.

(21) Appl. No.: 11/045,526

(22) Filed: Jan. 28, 2005

(65) Prior Publication Data

US 2009/0325234 A1 Dec. 31, 2009

Related U.S. Application Data

(60) Provisional application No. 60/540,225, filed on Jan. 28, 2004.

(51) Int. Cl.
*C12Q 1/68* (2006.01)
*C12P 19/34* (2006.01)

(52) U.S. Cl. .................... 435/6.12; 435/809; 435/303.1; 435/287.3; 435/304.1; 435/91.1; 435/91.2

(58) Field of Classification Search .................. 435/809, 435/303.1, 6.12, 287.3, 304.1, 91.2, 91.1
See application file for complete search history.

(56) References Cited

U.S. PATENT DOCUMENTS 4,683,195 A 7/1987 Mullis et al.
4,683,202 A 7/1987 Mullis
4,965,188 A 10/1990 Mullis et al.
5,075,216 A 12/1991 Innis et al.
5,176,203 A * 1/1993 Larzul ............................ 165/61
(Continued)

FOREIGN PATENT DOCUMENTS

WO WO 98/16313 * 4/1998
(Continued)

OTHER PUBLICATIONS

Hashimoto, M., et al., "Rapid PCR in a continuous flow device", *Lab Chip* 4:638-645, The Royal Society of Chemistry (Oct. 2004).

(Continued)

*Primary Examiner* — Nathan Bowers
(74) *Attorney, Agent, or Firm* — Stites & Harbison, PLLC; Terry L. Wright; David W. Nagle, Jr.

(57) ABSTRACT

A thermal cycle system and method suitable for mass production of DNA comprising a temperature control body having at least two sectors. Each sector has at least one heater, cooler, or other means for changing temperature. A path traverses the sectors in a cyclical fashion. In use, a piece of tubing or other means for conveying is placed along the path and a reaction mixture is pumped or otherwise moved along the path such that the reaction mixture is repetitively heated or cooled to varying temperatures as the reaction mixture cyclically traverses the sectors. The reaction mixture thereby reacts to form a product. In particular, polymerase chain reaction reactants may continuously be pumped through the tubing to amplify DNA. The temperature control body is preferably a single aluminum cylinder with a grooved channel circling around its exterior surface, and preferably has wedge-shaped or pie-shaped sectors separated by a thermal barrier.

23 Claims, 14 Drawing Sheets

U.S. PATENT DOCUMENTS

| | | | | |
|---|---|---|---|---|
| 5,270,183 | A | 12/1993 | Corbett et al. | |
| 5,415,839 | A | 5/1995 | Zaun et al. | |
| 5,508,197 | A | 4/1996 | Hansen et al. | |
| 5,736,314 | A * | 4/1998 | Hayes et al. | 435/4 |
| 5,849,208 | A | 12/1998 | Hayes et al. | |
| 6,033,880 | A * | 3/2000 | Haff et al. | 435/91.1 |
| 6,132,996 | A * | 10/2000 | Hunicke-Smith | 435/91.2 |
| 6,537,752 | B1 | 3/2003 | Astle | |
| 6,613,560 | B1 * | 9/2003 | Tso et al. | 435/287.2 |
| 6,632,653 | B1 | 10/2003 | Astle | |
| 6,709,692 | B2 | 3/2004 | Sudor | |
| 7,015,030 | B1 * | 3/2006 | Fouillet et al. | 435/287.1 |
| 7,133,726 | B1 | 11/2006 | Atwood et al. | |
| 2003/0017551 | A1 | 1/2003 | Parthasarathy et al. | |
| 2008/0038813 | A1 * | 2/2008 | Chen | 435/287.2 |
| 2009/0057147 | A1 * | 3/2009 | Kayyem | 204/403.01 |

FOREIGN PATENT DOCUMENTS

| | | |
|---|---|---|
| WO | WO 2005/075683 | 8/2005 |
| WO | WO 2008/045288 | 4/2008 |

OTHER PUBLICATIONS

Obeid, P.J., et al., "Microfabricated Device for DNA and RNA Amplification by Continuous-Flow Polymerase Chain Reaction and Reverse Transcription-Polymerase Chain Reaction with Cycle Number Selection", *Anal. Chem.* 75:288-295, American Chemical Society (Jan. 2003).

Takara Bio Incorporated, "Takara Bio to Produce DNA Fragments for DNA Microarrays on Industrial Scale", available online at http://www.japancorp.net/Article.Asp?Art_ID=2764 (2 pages) (May 2002).

Hunicke-Smith, "PCR and Cycle Sequencing Reactions: A New Device and Eng'g Model," Dissertation, May 1997; pp. i-200; Stanford U., USA.

Kopp et al., "Chemical Amplification: Continuous-Flow PCR on a Chip," Science, May 15, 1998, vol. 280; pp. 1046-1048.

Curcio et al., "Continuous Segmented-Flow Polymerase Chain Reaction for High-Throughput Miniaturized DNA Amplification," Analytical Chemistry, Jan. 1, 2003, vol. 75; pp. 1-7.

Berger et al., "Flow in Curved Pipes," Ann. Rev. Fluid Mech., 1983, vol. 15, pp. 461-512.

Takara Bio Inc., "Takara Bio to Produce DNA Fragments for DNA Microarrays on Industrial Scale," Japan Corporate News Network press release, May 7, 2002, available at http://www.japancorp.net/Article.Asp?Art_ID=2764.

ISA/US, International Search Report and Written Opinion for WO 2008/045288, completed Aug. 26, 2008.

Kim et al., "Fabrication and characterization of a PDMS-glass hybrid continuous-flow PCR chip," Biochemical Engineering Journal, 2006, vol. 29, pp. 91-97.

* cited by examiner

APPARATUS AND METHOD FOR A CONTINUOUS RAPID THERMAL CYCLE SYSTEM

CROSS-REFERENCE TO RELATED APPLICATIONS

This application claims the benefit of U.S. Provisional Application No. 60/540,225 filed Jan. 28, 2004.

STATEMENT REGARDING FEDERALLY SPONSORED RESEARCH OR DEVELOPMENT

The U.S. Government has a paid-up license in this invention and the right in limited circumstances to require the patent owner to license others on reasonable terms as provided for by the terms of Award No. 0314742 awarded by the National Science Foundation.

BACKGROUND OF THE INVENTION

1. Field of the Invention

The present invention relates to systems for maintaining multiple temperature regions, and in particular, to a device and associated method for the automated, bulk thermal cycling of fluids, solutions, and/or reactants.

2. Description of the Related Art

The polymerase chain reaction (PCR) is widely used by research professionals around the world as a means to amplify small strands of DNA. Typically, PCR is performed using automated thermal cyclers that alternately heat and cool numerous small tubes containing the PCR reaction mixture. Such a process uses a static reactor having discrete, confined spaces in which the reaction occurs when exposed to different temperatures in a repetitive sequence. This process is time intensive, labor intensive, and inefficient, as the tubes must be individually filled with the reactants, closed, processed through the automatic cycler, opened, and finally drained of the reaction product that contains the desired amplified DNA.

Accordingly, continuous thermal cyclers were developed to eliminate the need for using a multitude of small tubes to amplify DNA via PCR by using a dynamic reactor. Rather than using small tubes, continuous thermal cyclers use a constant or continuous stream of fluid repetitively passed through different temperature zones to amplify DNA. One example of a continuous thermal cycler is disclosed in U.S. Pat. No. 5,270,183 issued on Dec. 14, 1993, to Corbett et al. Corbett et al. disclose a device and method for DNA amplification in which a PCR reaction mixture is injected into a carrier fluid with which the PCR reaction mixture is immiscible, and the carrier fluid then passes through a plurality of temperature zones to facilitate DNA amplification within the PCR reaction mixture. The function of this device is to accelerate the processing of a multitude of different DNA strands contained in discrete pockets or plugs, hence the need for a carrier fluid that is immiscible with the PCR reaction mixture that acts to separate the different DNA strands. This device is not designed to produce mass quantities of DNA.

Moreover, the Corbett et al. device is not designed to be easily and quickly adaptable to different PCR reaction requirements. For example, the preferred arrangement for passing the carrier fluid through the temperature zones is to wrap tubing conveying the carrier fluid around separate cylinders maintained at different temperatures. Modifying the device for different reaction conditions therefore requires re-wrapping the tubing around one or more of the cylinders a different number of times, unwrapping the tubing around one or more of the cylinders to replace one or more of the cylinders with different cylinders, re-routing the tubing around the cylinders in different orders, or another such labor-intensive procedure. Additionally, efficiency and fine temperature control is reduced as the reaction mixture pockets pass from one cylinder to the next and thermal energy is unintentionally lost or gained at such "gaps."

Another example of a continuous thermal cycler is disclosed in Curcio, M. and Roeraade, J. (2003, published on web 2002) Continuous Segmented Flow Polymerase Chain Reaction for High-Throughput Miniaturized DNA Amplification, Anal. Chem. 75, 1-7. This device similarly is designed for numerous small sample mixtures separated by an immiscible fluid. Rather than using separate cylinders as different temperature zones as in the Corbett et al. device, however, this device uses separate thermally controlled water baths as temperature zones. This device is not designed for easy modification for providing a number of different reaction conditions, as additional water baths would have to be prepared and added for such modification. Use of this device also entails adding, checking, and draining water from the baths on a periodic basis, as well as cleaning of the water bath containers.

For the foregoing reasons, there is a need for a continuous thermal cycler that is designed to mass produce DNA strands, that is easily adaptable to different PCR reaction requirements, and that is efficient in operation.

SUMMARY OF THE INVENTION

The present invention comprises an apparatus and method for a continuous thermal cycle system capable of the bulk production of DNA strands that is efficient, scalable, easily adaptable to different PCR reaction requirements, and is relatively inexpensive to produce. An embodiment of the present invention has a plurality of temperature-controlled sectors within a temperature control body, thereby resulting in a plurality of temperature zones. A fluid preferably flows continuously through or along the apparatus via a path, and thereby through or along the different temperature zones.

A preferred embodiment of the present invention is particularly suited for amplification of DNA fragments quickly, easily, and in large quantities. Mass production of DNA at rates much greater than conventional DNA production rates is thereby effectively achieved using the present invention. Low manufacturing costs and enhanced scalability of the present invention permit relatively inexpensive, continuous amplification of DNA in bulk quantities. In particular, a preferred embodiment of the present invention comprises a single cylindrical temperature control body having twelve pie-shaped or wedge-shaped sectors, each sector having a means for obtaining a desired temperature, and each sector separated from other sectors by a thermal barrier. A grooved channel circles or spirals around the exterior surface of the temperature control body, and a length of tubing placed in or on the channel conveys DNA amplification reactants cyclically from one sector to subsequent sectors. The reactants are thereby exposed to different temperature zones in a cyclical fashion, ultimately resulting in the amplification of the DNA. A means for moving the reactants establishes the flow rate of the reactants through the length of tubing to optimize the amplification via PCR based upon the characteristics of the specific reactants. Any number of sectors may be incorporated into the temperature control body by simply dividing it into additional sectors or reducing the number of sectors. Also, further adaptability can be incorporated into the temperature control body by adding layered sectors and/or using a temperature control body having a shape other than a cylinder.

BRIEF DESCRIPTION OF THE FIGURES

The present invention is described with reference to the accompanying drawings. In the drawings, like reference numbers indicate identical or functionally similar elements.

DETAILED DESCRIPTION OF THE PREFERRED EMBODIMENTS

Figure 1:
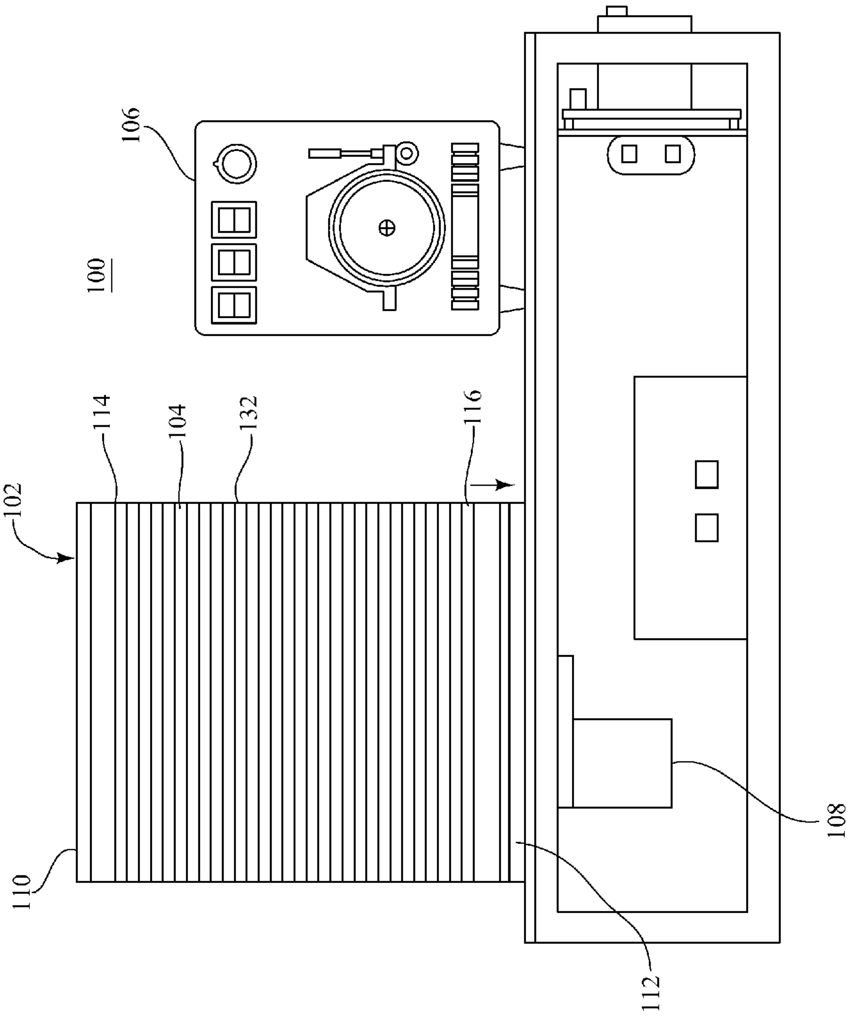
FIG. 1 is an elevation view of an embodiment of a thermal cycle system of the present invention.
Figure 2:
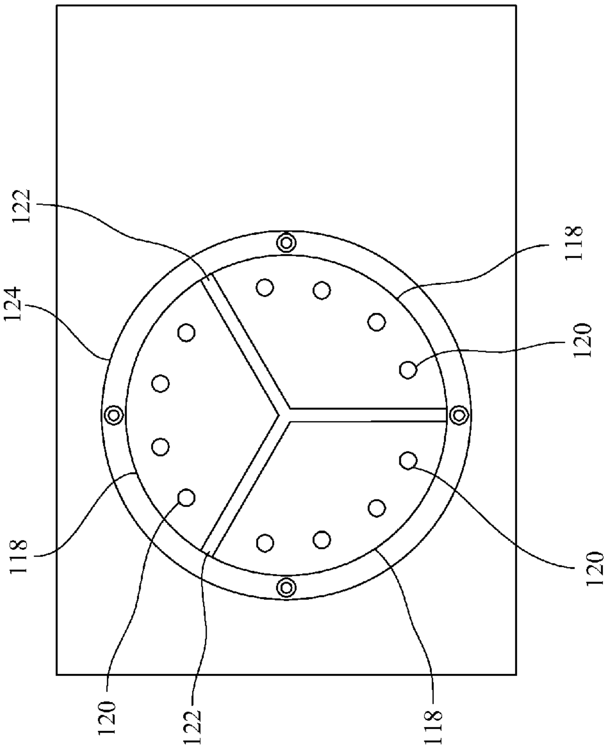
FIG. 2 is a plan view of the thermal cycle system of FIG. 1.
Figures 3A, 3B, 3C:
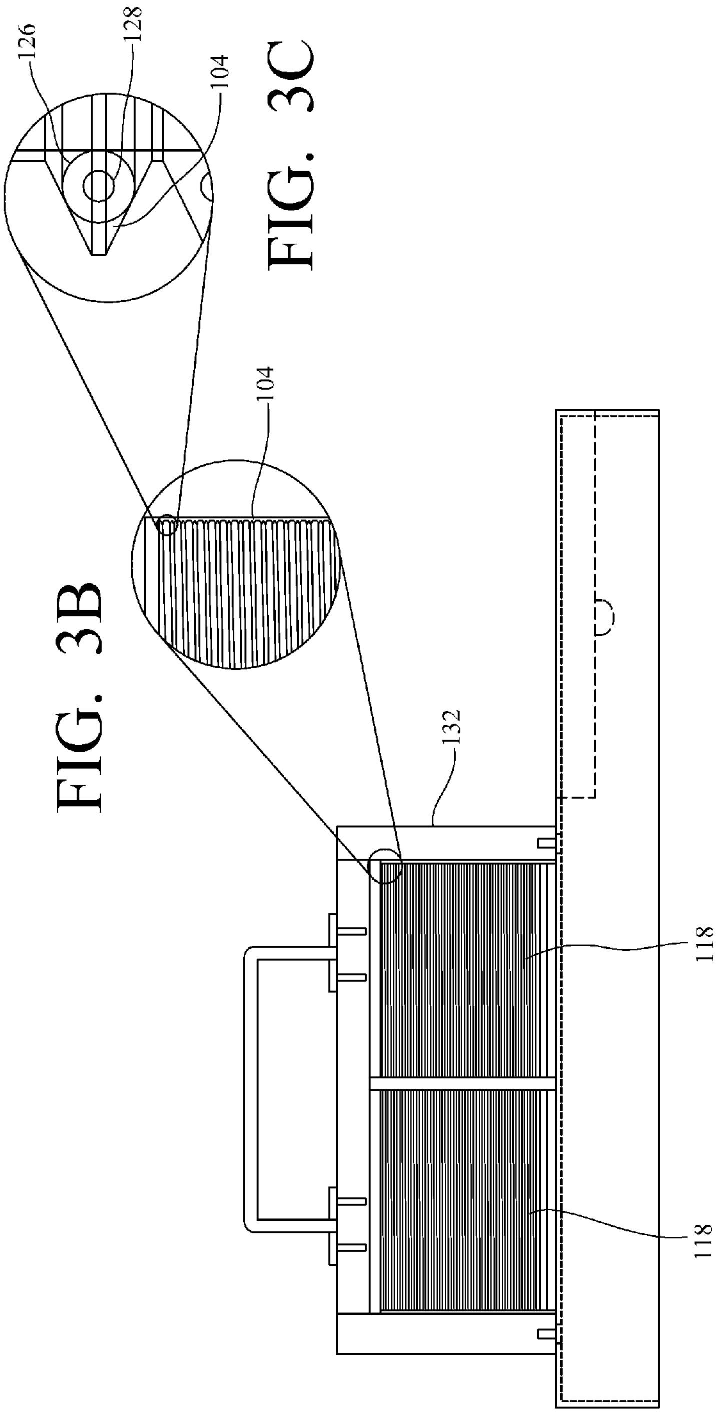
FIG. 3A is an elevation view of an alternate embodiment of the thermal cycle system of the present invention.
FIG. 3B is a expanded view of a portion of an exterior surface of the thermal cycle system of FIG. 3A.
FIG. 3C is an expanded view of a portion of a channel of the thermal cycle system of FIG. 3A.
Figure 4:
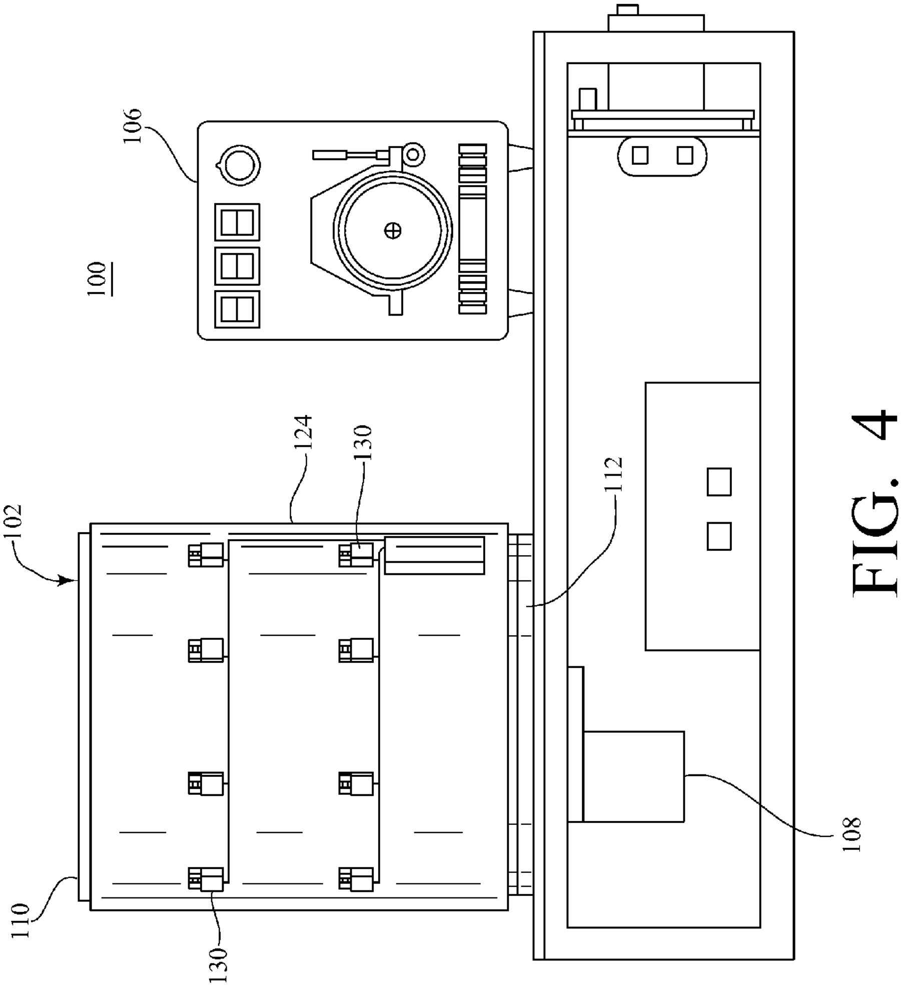
FIG. 4 is an elevation view of the thermal cycle system of FIG. 1 showing an insulating layer substantially surrounding the temperature control body.
Figure 5:
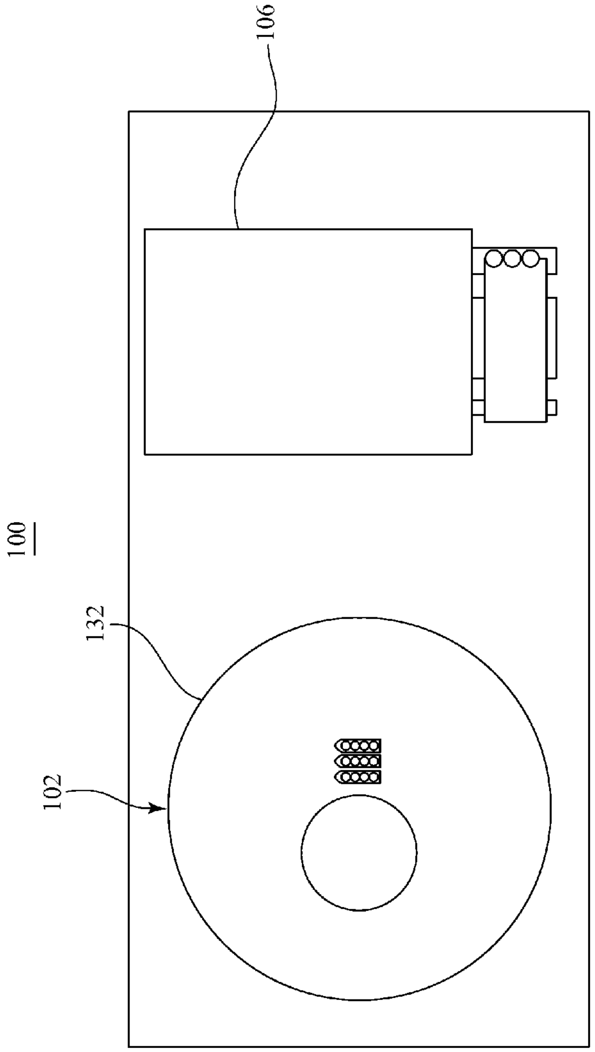
FIG. 5 is a top plan view of the thermal cycle system of FIG. 1.
Figure 6:
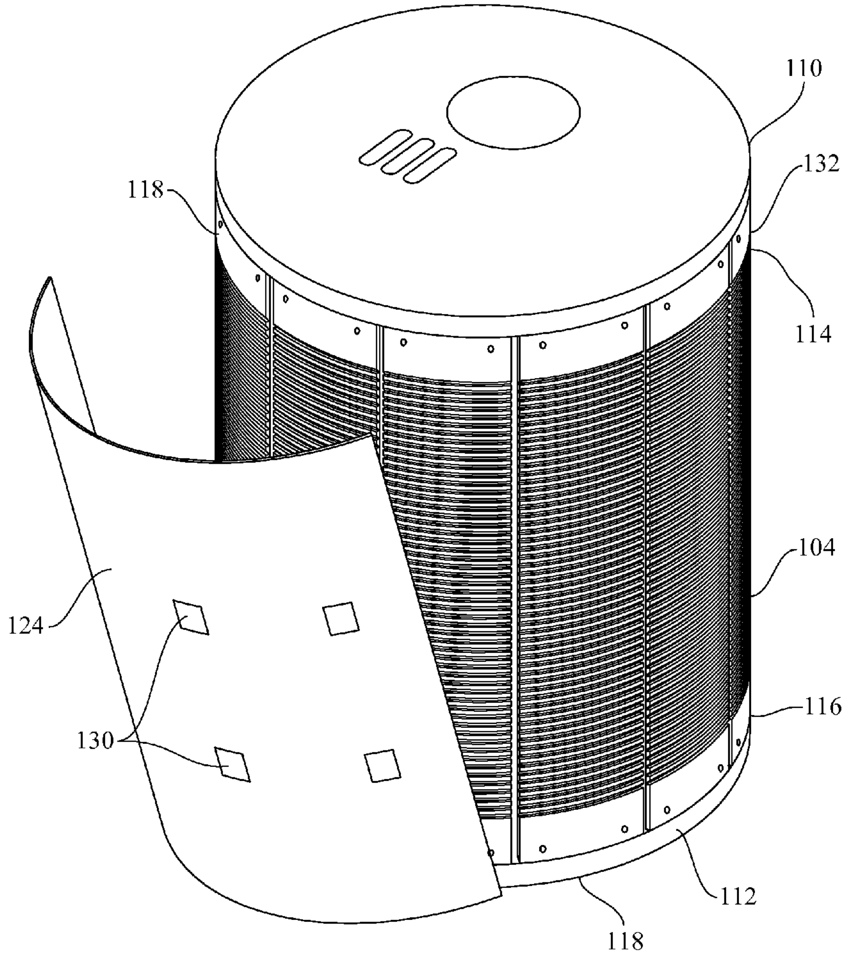
FIG. 6 is a perspective view of a temperature control body of the thermal cycle system of FIG. 1 showing a portion of an insulating layer.
Figure 7:
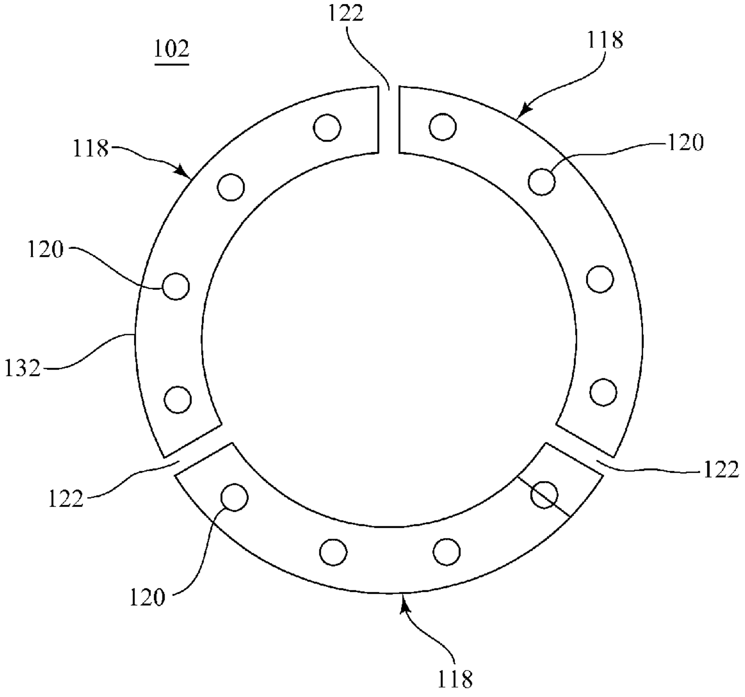
FIG. 7 is a top plan view of a temperature control body of the thermal cycle system of FIG. 1.
Figure 8:
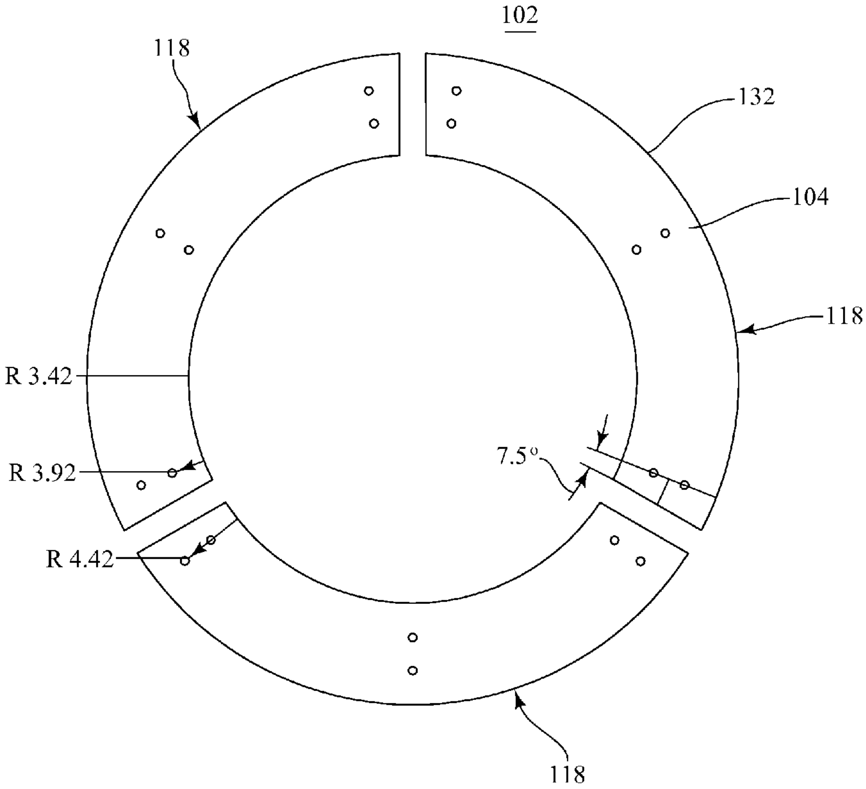
FIG. 8 is a bottom plan view of a temperature control body of the thermal cycle system of FIG. 1.
Figure 9:
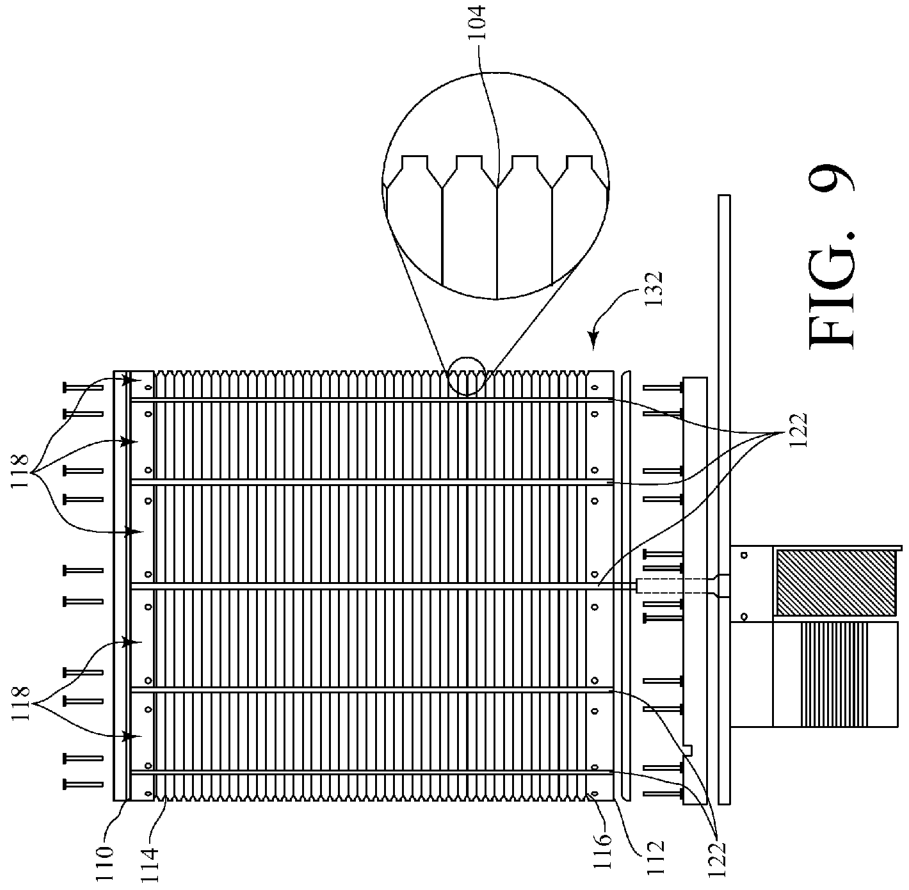
FIG. 9 is an elevation view of an alternate embodiment of the thermal cycle system of the present invention.
Figure 10:
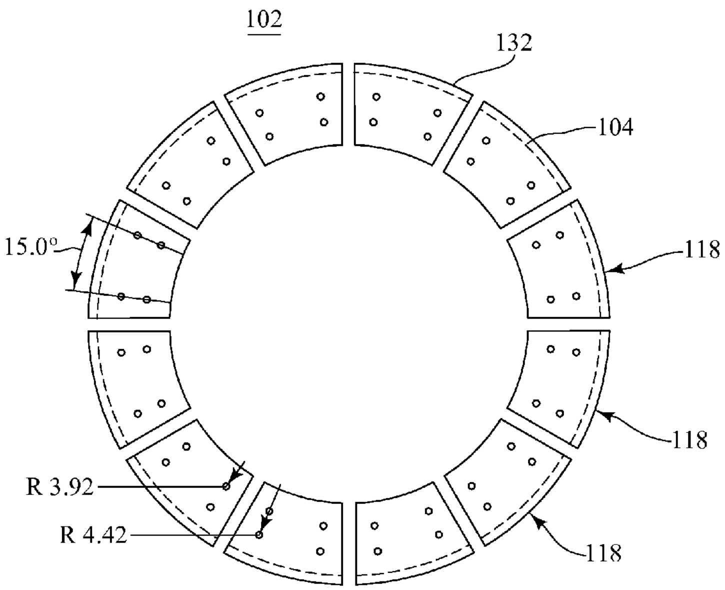
FIG. 10 is a top plan view of the thermal cycle system of FIG. 9.
Figure 11:
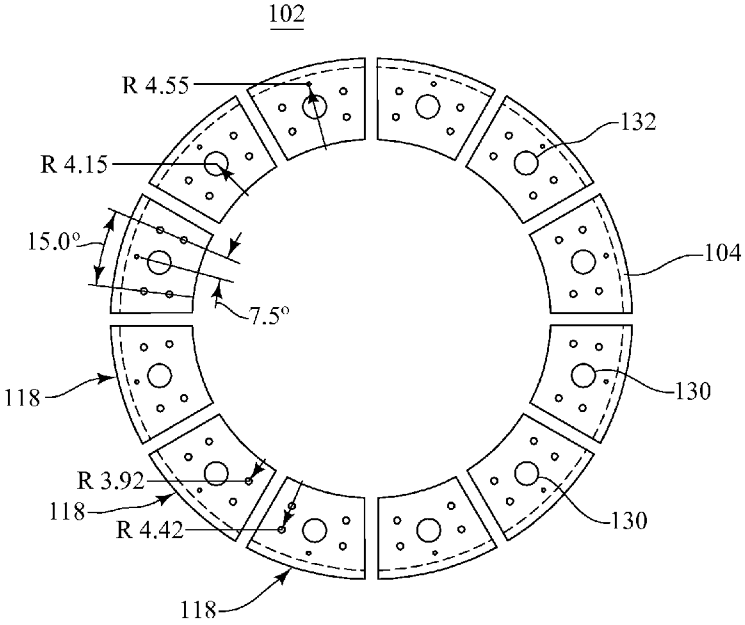
FIG. 11 is a bottom plan view of the thermal cycle system of FIG. 9.
Figure 12:
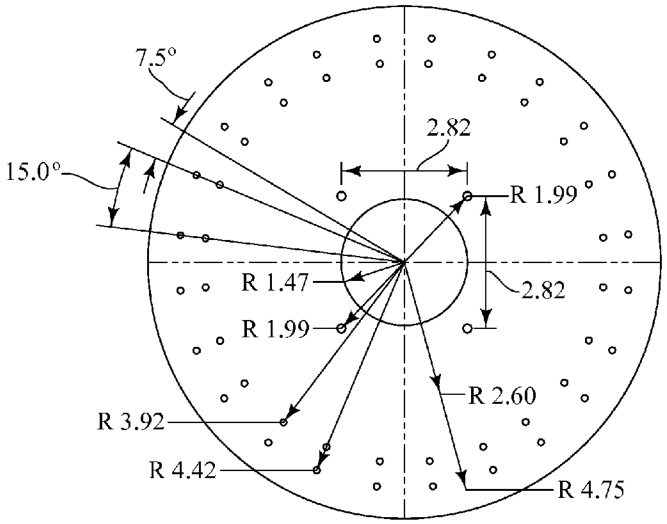
FIG. 12 is a plan view of a top cap of the thermal cycle system of FIG. 9.
Figure 13:
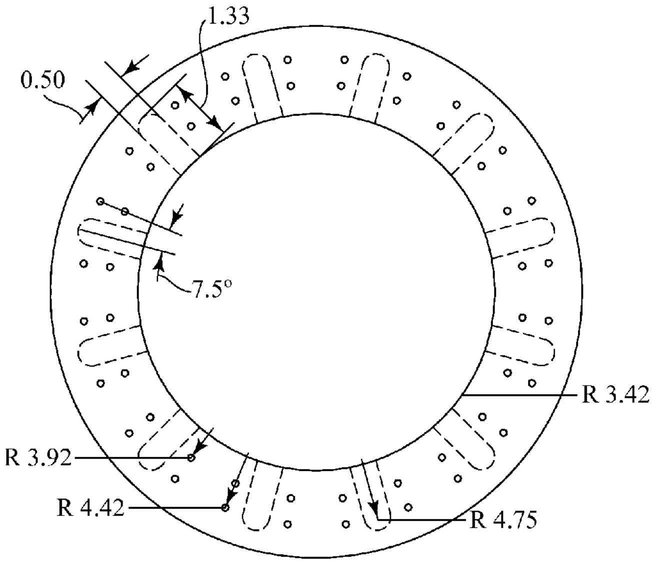
FIG. 13 is a plan view of a bottom cap of the thermal cycle system of FIG. 9.

The present invention is directed to an apparatus and method for simultaneously maintaining multiple temperature regions within a single physical structure. The present invention is therefore particularly suited for use in the automated thermal cycling of substances, such as those used in the amplification of nucleic acid sequences. With reference to the drawings, and in particular to FIGS. 1-13, a thermal cycle system 100 of the present invention preferably comprises a temperature control body 102 having at least two sectors 1 18 and a path 104 that cyclically passes from one initial sector 118 to each successive sector 118 in turn, thereafter returning to the initial sector 118 and cyclically repeating passes from one sector 118 to the next sector 118 as many times as is desired. The path 104 traverses the sectors 118 by passing along an exterior surface 132 of the temperature control body 102 from one sector 118 to each successive sector 118, by boring through the sectors 118 internally from one sector 118 to each successive sector 118, or by a combination of such external or internal travel.

Each sector 118 comprises at least one means for changing or obtaining a temperature 120. The means for changing temperature 120 is capable of achieving and maintaining a specific desired temperature. The means for changing temperature 120 is therefore preferably a heater, cooler, Peltier device, heat pump, oven, firebox, thermal reaction chamber, or similar means. Each sector 118 is preferably substantially made of aluminum, aluminum alloy, metal, metal alloy, a thermal conductor, an asymmetric thermal conductor, or combinations thereof. The means for changing temperature 120 thereby heats, cools, or maintains the temperature of the sector 118 such that the section of the path 104 located in or on each sector 118 is similarly heated, cooled, or maintained at the particular temperature of that sector 118.

Each sector 118 is also preferably separated from other sectors 118 by a thermal barrier 122 located between the sectors 118. The thermal barrier 122 may be passive, and may comprise a thermal insulator, air, gas, liquid, solid, and/or a combination thereof. The thermal barrier 122 may alternatively or additionally be an active device or material, such as a Peltier device, which can maintain a significant temperature differential. Each sector 118 therefore acts as an independent temperature sink wherein the means for changing temperature 120 for that sector 118 achieves and maintains a desired temperature throughout that sector 118, and a thermal barrier 122 thermally isolates each sector 118 from the other sectors 118. Multiple temperature regions are thereby efficiently achieved and maintained in a single body. An insulating layer 124 may optionally substantially surround the temperature control body 102 to minimize thermal transfer between the sectors 118 and the surrounding environment.

The temperature control body 102 may have any desired shape, such as a cylinder, cone, triangle, rectangle, pyramid, polygon, block, or cube. The sectors 118 may also have any desired shape conforming to sections, parts, or pieces of the temperature control body 102. For example, the sectors 118 may be wedge shaped, arc shaped, or pie-slice shaped, or may have the shape of sliced portions of a cylinder, cone, triangle, rectangle, pyramid, polygon, block, or cube. The sectors 118 may also be layered, one atop another. There may be any number of desired sectors 118. All the sectors 118 may be the same size, or one or more of the sectors 118 may be a different size.

The thermal cycle system 100 also preferably comprises a plurality of temperature sensors 130. Each sector 118 preferably has one or more temperature sensors 130 located within or adjacent to that sector 118 to measure the temperature within that sector 118 or portion of sector 118. Each temperature sensor 130 produces temperature values output that directly or indirectly represents the temperature of that sector 118. Such temperature sensors 130 may be any conventional instrument for determining temperature. Such temperature sensors 130 may optionally be placed in or on the insulating layer 124.

The thermal cycle system 100 also preferably comprises a means for regulating temperature 134. The means for regulating temperature 134 regulates each means for changing temperature 120, such that desired temperatures within each sector 118 are achieved. Any number of means for regulating temperature 134 may be used to regulate the means for changing temperature 120. The means for regulating temperature 134 preferably comprises a thermostat. In one embodiment, a computer system executing a software program is in communication with the means for changing temperature 120 and the temperature sensors 130, wherein the software uses a predefined set of target temperatures for each sector 118 for control and regulation of the means for changing temperature

120. The target temperatures are dictated by the desired application and use of the thermal cycle system 100, which in a preferred embodiment is PCR. The software receives the temperature values output from the temperature sensors 130. Each such temperature value represents directly or indirectly the temperature of a sector 118. The software compares the temperature value output of each sector 118 with its predefined target temperature for that sector 118. Then, if the temperature value output received from a temperature sensor 130 falls above or below a minimum predefined value, the software engages one or more of the means for changing temperature 120 in that sector 118 to increase or decrease the heat in that sector 118 or in an appropriate portion of that sector 118. That is, according to a temperature sensor's 130 value and position, the system may engage all or a subset of the means for changing temperature in the sector 118. Alternative means for regulating temperature 134 can be used such as any conventional thermostat system.

The thermal cycle system 100 also preferably comprises a means for moving 106 a fluid 128 along the path 104. The fluid 128 thereby cyclically passes from one sector 118 to another sector 118, and the temperature of the fluid 128 equilibrates with the temperature of the sector 118 through which or on which the fluid 128 is passing. The temperature of the fluid 128 thereby cyclically changes as it flows along the path 104. The fluid 128 preferably comprises any thermally dependent reaction mixture, reactants, or reagents. The fluid moving means 106 preferably comprises a pump, such as a peristaltic pump, a pressurized gas system, or similar means. For example, a pressurized helium system can be used to pump the fluid 128 along the path 104.

In a preferred embodiment of the thermal cycle system 100, the temperature control body 102 is a single substantially cylindrical body having a plurality of substantially pie-slice shaped or wedge-shaped sectors 118. The path 104 comprises a grooved channel circling or spiraling around the exterior surface 132 of the temperature control body 102. A length of tubing 126 is placed within or along the grooved channel. The desired temperature for each sector 118 is determined based upon the characteristics and requirements of a particular thermal-dependent reaction. The means for regulating temperature 134 and the means for changing temperature 120 are activated such that the desired temperature for each sector 118 is attained. The temperature sensors 130 measure the actual temperatures of each sector 118, and each means for changing temperature 120 is activated or inactivated as appropriate to attain and maintain the desired temperature for each sector 118. The fluid moving means 106 moves or pumps the fluid 128 through the length of tubing 126. The fluid 128 is thereby subjected to a series of different temperature regions on a cyclical basis that ultimately results in a transformation or reaction of the fluid 128 into a product or products. The temperature control body 102 may optionally be attached to a base for support. A means for rotating the temperature control body 102 may also optionally be used to facilitate placing the length of tubing 126 within or along the grooved channel. Such means for rotating may comprise an electric motor with wheel and gear assemblies or similar alternative.

The thermal cycle system 100 is particularly suited for large scale amplification of DNA via PCR. Thus, a preferred embodiment of the thermal cycle system 100 has grooved channel path 104 circling around the exterior surface 132 of a single cylindrical temperature control body 102. Thus, the channel has a first end 114 near the top edge 110 of the temperature control body 102 and a second end 116 near the bottom edge 112 of the temperature control body 102. The depth of the groove is discretionary and may depend on the diameter of the length of tubing 126 that can be placed within or along the groove and/or may depend on the particular application of the thermal cycle system 100. The cylindrical temperature control body has twelve equally sized arc-shaped sectors 118, and each sector 118 has one means for changing temperature 120. Each sector 118 has one temperature sensor 130, specifically a type K thermocouple, internally placed within the sector 118. A fluid moving means 106, preferably a pressurized helium system, moves a fluid 128 through the length of tubing 126. The fluid 128 preferably comprises a DNA strand to be amplified, two primers, and a heat stable Taq polymerase. Additional substances may be included in the fluid 128 to facilitate DNA amplification via PCR. A single means for regulating temperature 134 preferably regulates every means for changing temperature 120. The fluid moving means 106 moves the fluid 128 from sector 118 to sector 118 such that DNA amplification via PCR is optimized.

In one embodiment of the thermal cycle system 100, the cylindrical temperature control body 102 is divided into 3 equal pie-slice shaped sectors 118, and there are about 30 to about 40 "turns" of the channel around the cylinder with the preferred number being about 33 turns. Each "turn" of the channel is a "cycle" of the fluid 128 traveling around the circumference of the exterior surface 132 of the cylinder. Also, tubing 126, e.g., polytetrafluoroethylene (PTFE) tubing or TEFLON tubing or synthetic resinous fluorine-containing polymer tubing, within the channels is surrounded by 3 insulating layers 124 (one per sector 118), wherein each insulating layer 124 has eight temperature sensors 130. A peristaltic pump 106 is positioned about six to about seven inches from the point at which the tubing 126 extends away from the bottom 112 of the cylinder. Using this arrangement of the apparatus, the preferred method for using the present apparatus pumps the fluid 128 through the tubing 126 at a rate of about 45 seconds per sector 118 (temperature zone), resulting in a flow rate of about 135 seconds per cycle (1 "turn" of the tubing 126 around the cylinder).

The temperatures and cycle times imposed on the reagents by the sectors/temperature zones 118 are preferably consistent with the well-known and current process of PCR. The preferred use of the present apparatus and method for a continuous thermal cycle system is amplifying DNA, but this use of the present invention is for convenience purposes only. It would be readily apparent to one of ordinary skill in the relevant art to use the apparatus and method of the present invention in a different application requiring the continuous heating or cooling of a fluid 128 through multiple temperature zones.

The fluid 128 may be mixed or created in a large batch prior to its introduction into the length of tubing 126, or the fluid 128 may be created just-in-time or on-the-fly right before it is introduced into the length of tubing 126. The fluid 128 is preferably a substantially homogeneous temperature-dependent reaction mixture, and there is preferably a continuous supply of such fluid 128 through the length of tubing 126. A means for controlling the introduction of the fluid 128 maybe used, such as a computer system and software program. The software program preferably uses a predefined protocol for determining the proper mix (by proportions), sequential order, and timing for inputting the fluid 128, and/or the fluid components, into the length of tubing 126. In one embodiment, the protocol for introducing the fluid 128 components is determined by particular PCR requirements. Any means for introduction of the fluid 128 may be used, such as a pump and valve manifold or network known to those skilled in the art.

The resulting fluid 128 output from an end of the tubing is collected by conventional means. In a preferred embodiment, the resulting fluid contains amplified DNA. In addition, it is readily apparent that the apparatus and method of the present invention will provide a continual supply of amplified DNA so long as the pump is feeding the fluid components through the apparatus as described herein.

A method of the present invention for the facilitation of a chemical reaction requiring cyclical temperature changes therefore comprises activating a means for changing temperature 120 on a thermal cycle system 100 having a means for conveying a fluid such as a length of tubing 126 extending along a path 104, introducing a substantially homogeneous temperature-dependent reaction mixture into the means for conveying, activating a means for moving 106 such that the reaction mixture moves through the means for conveying and such that the reaction mixture reacts to form a product, and collecting the product at an end of the means for conveying. The chemical reaction is preferably a polymerase chain reaction. The method optionally further comprises continuously replenishing the fluid at one end of the means for conveying.

EXAMPLE

A sample was prepared containing: 12% MgC12 (25mM), 0.33% Taq DNA polymerase (5 units/µl), 2.0% dNTP's (deoxyadenosine triphosphate (dATP), deoxycytidine triphosphate (dCTP), deoxyguanosine triphosphate (dGTP) and deoxythymidine triphosphate (dTTP)), 8.0% template (2 µg/ml), 61.66% PLURONIC® F108 solution (1.5% solution; PLURONIC® is a registered trademark of BASF Corporation of Mount Olive, N.J.), 4% forward primer, 4% reverse primer, 8% reaction buffer (10X concentration). The solution can be scaled up to the correct volume using these figures. The twelve vertical sectors 118 of the cylindrical temperature control body 102 were heated to three different temperatures, four adjacent sectors 118 were heated to 95° C., another four adjacent sectors were heated to 59° C., and the final four adjacent sectors 118 were heated to 72° C. 1/32" ID, 1/16" OD TEFLON® PTFE tubing (TEFLON® is a registered trademark of E.I. Dupont De Nemours Company of Wilmington, Delaware) was wrapped around the temperature control body 102 thirty times to subject the length of tubing 126 and reaction mixture to the three different temperatures thirty different times in succession. The reaction mixture was then pumped through this tubing 126 using a pressurized vessel at 20 PSI. After the reaction mixture was fed to the temperature control body 102, mineral oil was used to push the sample through the entire length of tubing 126. The flow rate of the reaction mixture was controlled with a flow valve to 0.25 ml/min. The specific DNA sequence (whose limits are defined by the oligonucleotide primers) present in the sample was amplified as it passed cyclically through the temperature zones. After the thirtieth cycle, the tubing 126 exited the cylinder 102, and the contents were collected. The sample was then analyzed on a Cambrex Reliant Precast 2% Agarose Gel and stained with ethidium bromide.

Figure 14:
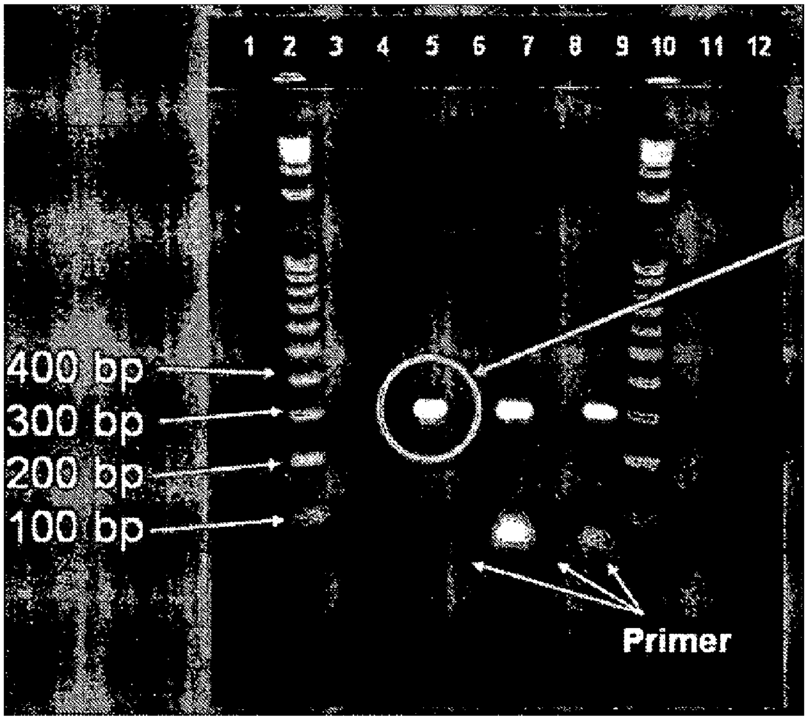
FIG. 14 is a photograph of an electrophoresis gel demonstrating the efficiency of an embodiment of the thermal cycle system of the present invention as compared with the efficiency of a conventional system.

An image of the gel was acquired using a BIORad Geldoc EQ system and is shown in FIG. 14. The lane contents were as follows: lane 1 empty; lane 2 ladder; lane 3 no template negative control (sample A); lane 4 empty; lane 5 sample amplified in an embodiment of the thermal cycle system 100 (sample B); lane 6 empty; lane 7 sample amplified in an embodiment of the thermal cycle system 100 followed by amplification in a conventional Perkin Elmer 480 machine (sample C); lane 8 empty; lane 9 positive control sample run with the conventional Perkin Elmer 480 machine (sample D); lane 10 ladder; lane 11 empty; and lane 12 empty.

The image was analyzed using ImageJ version 1.33u software wherein intensity data was extracted to obtain integrated intensities and calculations included a background subtraction, and no other normalization. The band intensity for sample A was 0.07, the band intensity for sample B was 3.62, the band intensity for sample C was 3.77, and the band intensity for sample D was 3.19.

This data indicates that the system and method of this invention is as efficient, if not more efficient, than an example of a standard commercial system, a Perkin Elmer 480 machine. Three identical reaction mixtures were prepared and one sample was examined in its unamplified form without template (sample A), one sample was run with the system of this invention (sample B), one sample was first run with the system of this invention and then run through a conventional commercial system (sample C), and one sample was run on a conventional commercial system (sample D). The intensity of the band on a gel at the targeted mass (300 bp) is an indicator of the quantity of DNA product produced.

Sample C produced the most intense band, but it is not very much more intense than the sample produced by this invention alone. Since sample C was subjected to thirty cycles with an embodiment of the thermal cycle system 100, then with thirty cycles of a commercial system, it is reasonable to expect some additional amplification if active reagents remain after exiting the machine of the present invention.

Sample B, the DNA produced using the machine of this invention, produced the second most intense band. Sample D is included to demonstrate the relative quantity of DNA to be expected from a conventional commercial system, the Perkin Elmer system. The band from the commercial system, sample D, is less intense than the band from the system and method of this invention, sample B. This means that the system and method of this invention is equal or better in efficiency than the commercial system. Sample A is used to indicate that no DNA (or a negligible amount of signal) is observed in a system subjected to amplification conditions (in the Perkin Elmer commercial system) but lacking template DNA, that there is not a contaminant in the reaction solution which could be misinterpreted as amplification. The important feature of this data is the fact that the sample B band is more intense (indicating a better reaction) than the same reaction carried out on the conventional system.

CONCLUSION

While various embodiments of the present invention have been described above, it should be understood that they have been presented by way of example only, and not limitation. It will be understood by those skilled in the art that various changes in form and details may be made therein without departing from the spirit and scope of the invention as defined in the appended claims. Thus, the breadth and scope of the present invention should not be limited by any of the above-described exemplary embodiments, but should be defined only in accordance with the following claims and their equivalents.

What is claimed is:

1. A method for the facilitation of a chemical reaction requiring cyclical temperature changes for production of a product, comprising:

activating one or more means for changing temperature on a thermal cycle system, wherein said thermal cycle system comprises a temperature control body comprising an exterior surface, at least two sectors forming a portion of said exterior surface, and a path cyclically passing through said sectors, wherein each sector comprises at least one of said means for changing temperature and is an independent temperature sink, a tubing for conveying a fluid having a length, a first end, and a second end, said tubing further defining a volume and said tubing extending along said path, and a means for moving in communication with said tubing, wherein said means for moving is adapted for moving said fluid through said tubing;

introducing a fluid, which is a substantially homogeneous temperature-dependent reaction mixture, into said tubing;

activating said means for moving such that said reaction mixture moves through said tubing, and such that said reaction mixture reacts to form a product;

continuously replenishing said reaction mixture at the second end of said tubing while said means for moving is activated so that said reaction mixture is continuously conveyed through the length of said tubing, so that said reaction mixture fills the entire volume of said tubing along the length of said tubing from the second end to the first end, and so that said reaction mixture is conveyed without impediment from the second end to the first end; and collecting a continual supply of said product at the first end of said tubing so long as said means for moving is activated.

2. The method of claim 1, wherein said chemical reaction is a polymerase chain reaction.

3. The method of claim 2, wherein said substantially homogeneous temperature-dependent reaction mixture contains a non-ionic surfactant.

4. The method of claim 1, wherein said path is a grooved channel on said exterior surface of said temperature control body.

5. A method for the facilitation of a chemical reaction requiring cyclical temperature changes for production of a product, comprising:

controlling temperatures of at least twelve sectors so as to achieve a target temperature for each sector, wherein each sector is an independent temperature sink substantially made of a solid material and constitutes a respective portion of a single temperature control body;

conveying a temperature-dependent reaction mixture along a path through a tubing having a length, a first end, and a second end, said tubing further defining a volume, with the path passing through the at least twelve sectors repeatedly for several consecutive cycles, wherein for each cycle, the path passes once through a width of a first sector, and passes once through a width of one or more successive sectors, before returning to the first sector;

continuously replenishing said reaction mixture into the second end of said tubing such that said reaction mixture is continuously conveyed through said tubing, such that said reaction mixture fills the entire volume of said tubing along the entire length of said tubing from the second end to the first end, and such that said reaction mixture is conveyed without impediment from the second end to the first end; and collecting a continual supply of said product at the first end of said tubing.

6. The method of claim 5, wherein the step of controlling temperatures includes:

setting the target temperature or temperature gradient range for each sector;

monitoring the temperature of each sector; and adjusting the temperature of each sector to achieve and maintain its respective target temperature.

7. The method of claim 6, wherein the step of setting the target temperature or temperature gradient range for each sector includes setting the equivalent target temperature for at least two successive sectors.

8. The method of claim 5, wherein the single temperature control body has an exterior surface, each sector forming a portion of the exterior surface, wherein the path is a grooved channel on the exterior surface.

9. The method of claim 5, wherein the path is a channel formed internally within the temperature control body so as to pass internally through the sectors.

10. The method of claim 5, wherein the temperature control body is a cylinder having a circumference, wherein each sector is wedge-shaped, and wherein the path is a channel that spirals around the circumference of the cylinder.

11. The method of claim 5, wherein the width of each sector is substantially equivalent in size.

12. The method of claim 5, wherein the shape of said temperature control body is a three-dimensional shape of a geometrical form selected from the group consisting of a polygon, cone, and pyramid.

13. The method of claim 5, wherein the temperature control body further comprises a thermal barrier between the sectors.

14. The method of claim 5, wherein said chemical reaction is a polymerase chain reaction.

15. A method for continuously regulating temperature of a fluid for production of a product, comprising:

dispensing a reaction mixture into a tubing having a first end, a second end, and a length, and said tubing further defining a volume, wherein the first end of said tubing extends from a first end of a channel and the second end of said tubing extends from a second end of said channel, said reaction mixture being dispensed into the second end of said tubing, wherein said channel spirals around a perimeter of a temperature control body comprising at least two sectors that each form a portion of the perimeter, wherein each sector has at least one temperature control means and is substantially made of a solid material so as to be configured to operate as an independent temperature sink;

conveying said reaction mixture through said tubing from the second end of said tubing to the first end of said tubing;

determining a temperature of said tubing as said reaction mixture flows through said tubing across each said sector of said temperature control body;

regulating said at least one temperature control means of each sector based on the determined temperature so as to achieve a target temperature for the sector;

continuously replenishing said reaction mixture into the second end of said tubing so that said reaction mixture is continuously conveyed through the length of said tubing, so that said reaction mixture fills the entire volume of said tubing along the length of said tubing from the second end to the first end, and so that said reaction mixture is conveyed without impediment from the second end to the first end; and collecting a continual supply of said product at the first end of said tubing so long as the reaction mixture is being conveyed through said tubing.

16. The method of claim 15, wherein said temperature control body is a cylinder having a circumference, wherein each sector is wedge-shaped, and wherein said channel spirals around the circumference of the cylinder by one of (i) boring through said sectors internally from one sector to each successive sector, (ii) passing along the exterior surface of the cylinder from one sector to each successive sector, and (iii) alternating between boring through one or more successive sectors and passing along the exterior surface of the cylinder so as to traverse one or more successive sectors.

17. The method of claim 15, wherein said temperature control body is a cylinder having a circumference and a longitudinal axis, wherein the sectors are split into discontinuous layers, each sector being split along a plane perpendicular to the longitudinal axis so that successive sectors are layered adjacent to one another along the longitudinal axis of the cylinder.

18. The method of claim 15, wherein said first end of said channel terminates near a top edge of said temperature control body and said second end of said channel terminates near a bottom edge of said temperature control body.

19. The method of claim 15, wherein each sector is substantially made of a thermal conductor.

20. The method of claim 19, wherein said thermal conductor is selected from the group consisting of aluminum, aluminum alloy, metal, alloy, ceramic, and combinations thereof.

21. The method of claim 15, wherein said temperature control body is surrounded with at least one insulating layer.

22. A method for the facilitation of a chemical reaction requiring cyclical temperature changes for production of a product, comprising:

activating one or more means for changing temperature on a thermal cycle system, wherein said thermal cycle system comprises a temperature control body comprising an exterior surface, at least two sectors forming a portion of said exterior surface, and a path cyclically passing through said sectors, wherein each said sector comprises at least one of said means for changing temperature and is an independent temperature sink, a tubing for conveying a fluid having a length, a first end, and a second end, said tubing further defining a volume and extending along said path, and a pump for moving said fluid through said tubing;

introducing a fluid, which is a substantially homogeneous temperature-dependent reaction mixture that includes a non-ionic surfactant, into said tubing;

activating said pump such that said reaction mixture moves through said tubing, and such that said reaction mixture reacts to form a product;

continuously replenishing said reaction mixture at the second end of said tubing while said pump is activated so that said reaction mixture is continuously conveyed through the length of said tubing, so that said reaction mixture fills the entire volume of said tubing along the length of said tubing from the second end to the first end, and so that said reaction mixture is conveyed without impediment from the second end to the first end; and collecting a continual supply of said product at said first end of said tubing so long as said pump is activated.

23. The method of claim 5, wherein said chemical reaction is a polymerase chain reaction.

* * * * *